United States Patent
Sai et al.

(10) Patent No.: US 12,070,322 B2
(45) Date of Patent: Aug. 27, 2024

(54) METHOD FOR DETERMINING SKIN CONDITION BASED ON THERMAL SENSITIVITY IN SKIN

(71) Applicant: Shiseido Company, Ltd., Tokyo (JP)

(72) Inventors: Ki Sai, Kanagawa (JP); Shigeyoshi Fujiwara, Kanagawa (JP); Hirofumi Aoki, Kanagawa (JP); Takeshi Hariya, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 1007 days.

(21) Appl. No.: 16/966,281

(22) PCT Filed: Jan. 28, 2019

(86) PCT No.: PCT/JP2019/002804
§ 371 (c)(1),
(2) Date: Jul. 30, 2020

(87) PCT Pub. No.: WO2019/151197
PCT Pub. Date: Aug. 8, 2019

(65) Prior Publication Data
US 2020/0367804 A1    Nov. 26, 2020

(30) Foreign Application Priority Data

Jan. 30, 2018    (JP) .................................. 2018-014007

(51) Int. Cl.
*A61B 5/00*    (2006.01)
*A61B 5/01*    (2006.01)

(52) U.S. Cl.
CPC ................ *A61B 5/443* (2013.01); *A61B 5/01* (2013.01); *A61B 2562/0271* (2013.01)

(58) Field of Classification Search
CPC ... A61B 5/443; A61B 5/01; A61B 2562/0271; A61B 5/444; A61B 5/445; A61B 5/446; A61B 5/442; A61B 5/441; A61B 5/4875; A61B 5/4869; A61B 5/015; A61K 8/96; A61Q 17/00; A61Q 19/007
See application file for complete search history.

(56) References Cited

U.S. PATENT DOCUMENTS

| | | | |
|---|---|---|---|
| 2011/0112431 A1* | 5/2011 | Golosarsky | A61B 5/4827 600/555 |
| 2011/0313314 A1* | 12/2011 | Gefen | A61B 5/441 600/555 |
| 2015/0335279 A1* | 11/2015 | Mihara | A61B 5/443 600/306 |

FOREIGN PATENT DOCUMENTS

WO    WO-2012/146925    11/2012

OTHER PUBLICATIONS

Han "Diabetic and Sympathetic Influences on the Water Permeability Barrier Function of Human Skin as Measured using Transepidermal Water Loss" Published Nov. 2017 by NIH, pp. 1-6 (Year: 2017).*

(Continued)

*Primary Examiner* — Devin B Henson
*Assistant Examiner* — Matthew Eric Ogles
(74) *Attorney, Agent, or Firm* — Foley & Lardner LLP

(57) ABSTRACT

The purpose of the present invention is to develop a method or system for measuring the skin condition easily and accurately. The method for determining the skin condition based on the thermal sensitivity in the skin was perfected by discovering that the skin condition, especially the skin barrier function, can be determined based on the thermal sensitivity in the skin.

7 Claims, 6 Drawing Sheets

(56) References Cited

OTHER PUBLICATIONS

Grice "The Relationship of Transepidermal Water Loss to Skin Temperature in Psoriasis and Eczema" Published 1975 by the Journal of Investigative Dermatology, pp. 1-3 (Year: 1975).*

Encyclopedia of Cosmetics, The Society of Cosmetic Chemists of Japan, p. 439, "Transepidermal water loss," with partial English translation.

Kumamoto et al., "Japanese Cedar (Cryptomeria japonica) pollen allergen induces elevation of intracellular calcium in human keratinocytes and impairs epidermal barrier function of human skin ex vivo," Arch. Dermatol. Res., 2016, 308:49-54.

* cited by examiner

FIG. 5
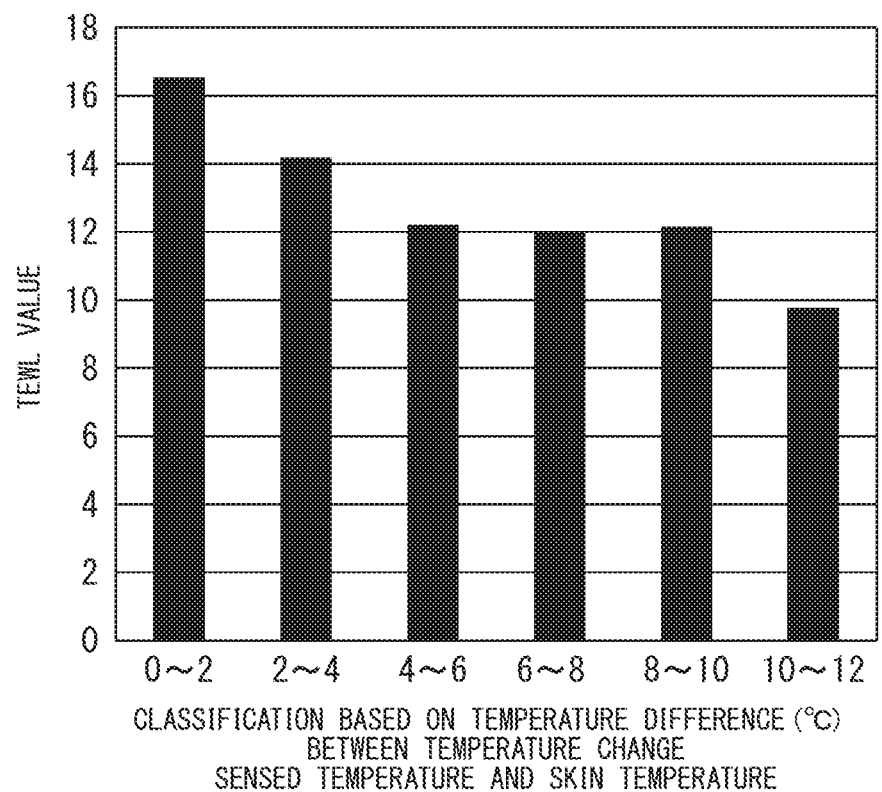
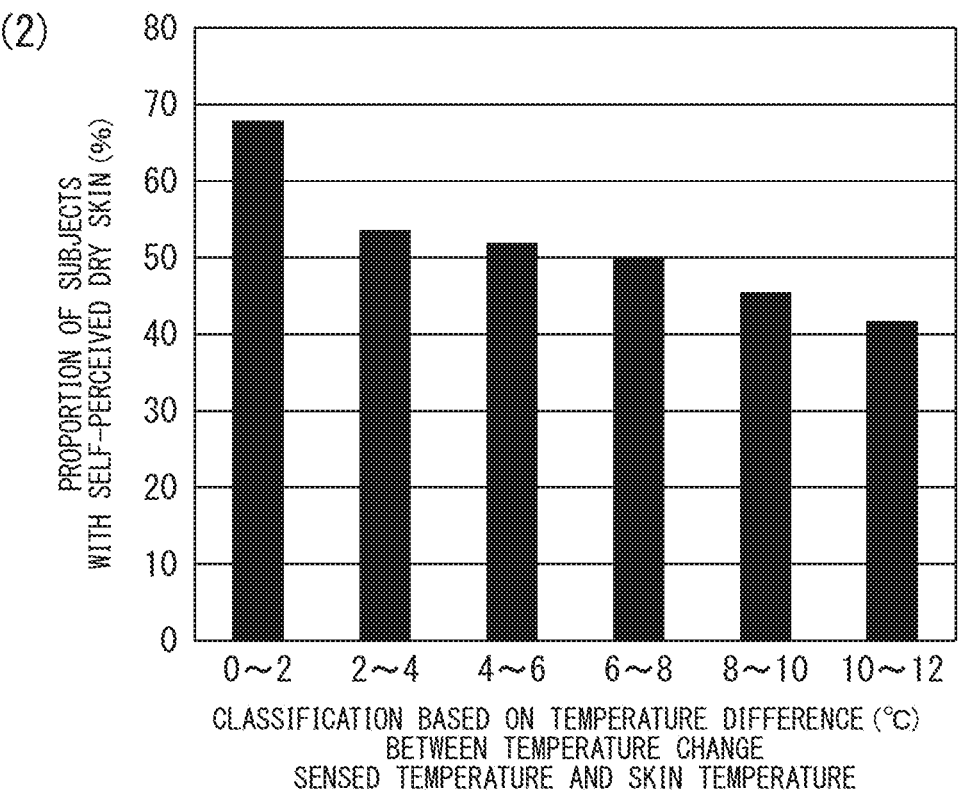

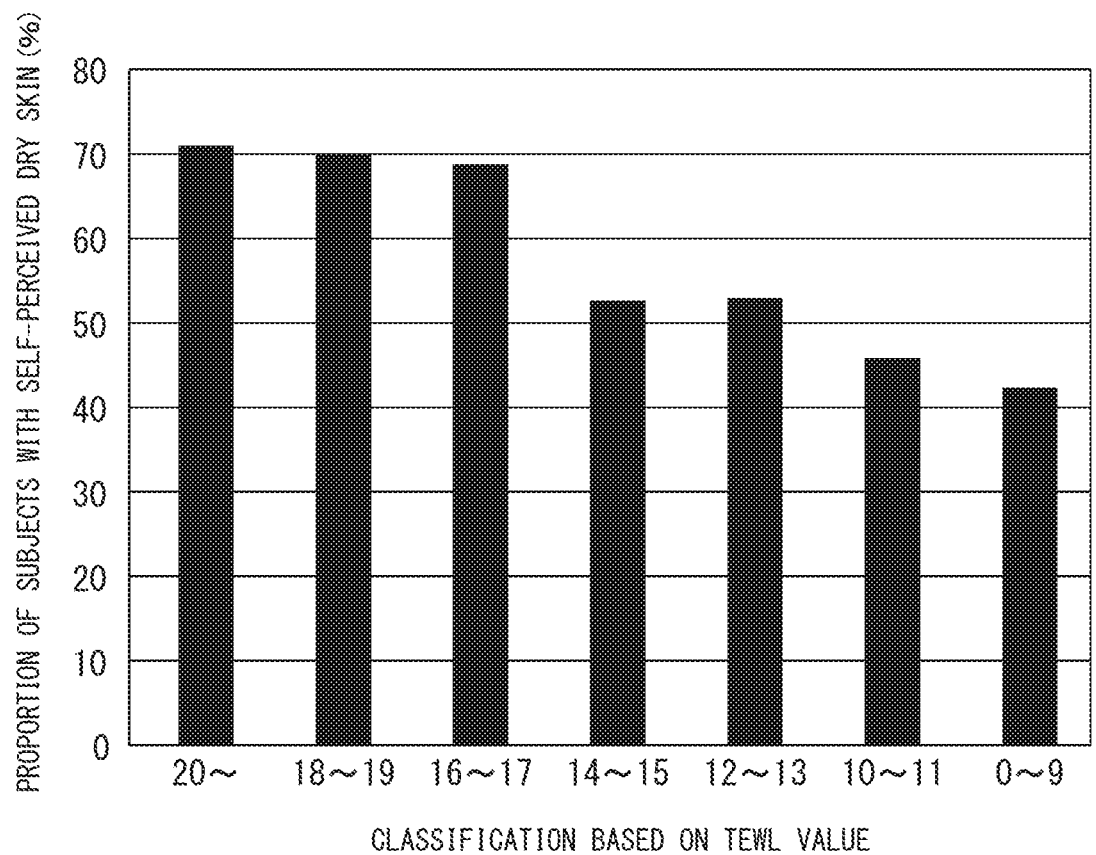

METHOD FOR DETERMINING SKIN CONDITION BASED ON THERMAL SENSITIVITY IN SKIN

CROSS-REFERENCE TO RELATED APPLICATIONS

This application is the U.S. National Stage of PCT/JP2019/002804, filed Jan. 28, 2019, which claims priority to JP 2018-014007, filed Jan. 30, 2018.

TECHNICAL FIELD

The present invention relates to the technical field of determining skin condition.

BACKGROUND ART

The skin exists as the outermost layer of the body and so is always exposed to external stimuli. The external stimuli include physical stimuli such as wounds, ultraviolet rays, and temperature, as well as stimuli from chemicals and antigenic substances. As a result of such stimuli, the condition of the skin, particularly skin barrier function, is greatly affected. The skin barrier function can be measured mainly through transepidermal water loss (TEWL). The higher the TEWL value, the more the skin barrier function decreases. It is considered that skin barrier function is affected by keratinization of keratinocytes, intercellular lipids, natural moisturizing factors, etc. In normal skin, keratin fibers aggregate with filaggrin in the process of keratinization of epidermal keratinocytes, and intercellular lipids such as ceramides, cholesterol, and fatty acids, and natural moisturizing factors are secreted extracellularly. It is considered that the keratinization process of keratinocytes contributes to the skin barrier function. Skin barrier function is reduced by physical stimuli such as scratches, contact with cold water or cold air and dryness, and is also reduced by exposure to chemicals and antigenic substances. For example, cedar pollen, which causes hay fever, reduces lamellar granules containing intercellular lipids such as ceramides, cholesterol, and fatty acids, through the activation of the PAR2 protein which is a membrane protein expressed in epidermal cells, and thereby causes a reduction in skin barrier function (NPTL 1: Arch Dermatol Res 308:49-54, 2016).

TEWL measurement methods include mainly the open system and closed system measuring methods. The open system measuring method directly measures the humidity on the surface of the skin whereas the closed system measuring method measures the water content by circulating dried air or nitrogen gas on the surface of the skin. Therefore, TEWL cannot be accurately measured under conditions that cause perspiration and it is recommended that measurements are carried out under constant temperature and humidity, and windless conditions. Furthermore, it has been difficult to measure an accurate value for TEWL since the measurement is easily affected by physiological conditions other than skin barrier functions, for example, skin water content (NPTL 2: Encyclopedia of Cosmetics, page 439; http://www.sccj-ifscc.com/terms/detail.php?id=35). Specifically, even if the skin barrier function is the same, when the skin water content is low, there is a tendency for the amount of water transpiration to be low, and thereby the skin barrier function is judged to be high, whereas when the skin water content is high, there is a tendency for the amount of water transpiration to be high, and thereby the skin barrier function is judged low.

CITATION LIST

Non Patent Literature

NPL 1: Arch Dermatol Res., 308, 49-54 (2016)
NPL 2: ENCYCLOPEDIA OF COSMETICS (The Society of Cosmetic Chemists of Japan), page 439

SUMMARY OF INVENTION

Technical Problem

There has been a demand for the development of a method for simply and accurately measuring skin condition based on a principle different from the TEWL method used to measure skin barrier function.

Solution to Problem

As a result of extensive research carried out by the present inventors regarding methods for measuring skin condition, it was found that by using thermal sensitivity in skin as an index, the skin condition, in particular, skin barrier function could be determined, and thereby the present invention was achieved.

Specifically, the present invention relates to the following invention:

[1] A method for determining skin condition using thermal sensitivity in skin as an index.

[2] The method for determining skin condition according to item [1] wherein the thermal sensitivity is determined from the temperature difference between the temperature at the time of sensing a temperature change and skin temperature.

[3] The method for determining skin condition according to item [2] wherein the skin condition is determined on the basis of a predetermined relationship between temperature difference and skin condition.

[4] The method for determining skin condition according to any one of items [1] to [3] wherein the skin condition is expressed by transepidermal water loss.

[5] The method for determining skin condition according to any one of items [1] to [4] wherein the skin condition is skin barrier condition.

[6] The method for determining skin condition according to any one of items [1] to [5] wherein the thermal sensitivity is sensitivity to temperatures higher than skin temperature.

[7] A system for determining skin condition comprising a variable temperature probe, a data processing unit, an input unit, and an output unit, wherein:
 the probe changes in temperature from a preset temperature;
 the input unit receives a signal indicating that a temperature change has been sensed;
 the data processing unit determines the skin condition on the basis of the temperature of the probe at the time of inputting the signal; and
 the output unit outputs the skin condition.

[8] The system according to item [7] wherein the preset temperature is skin temperature.

[9] The system according to item [7] or [8] wherein the skin condition is determined on the basis of the temperature difference between determined temperature and the skin temperature.

[10] The system according to item [9] wherein the data processing unit determines the skin condition based on a predetermined relationship between temperature difference and skin condition.

[11] The system according to any one of items [7] to [10] wherein the skin condition is expressed by transepidermal water loss.

[12] The system according to any one of items [7] to [11] wherein the skin condition is skin barrier condition.

[13] The system according to any one of items [7] to [12] wherein the thermal sensitivity is sensitivity to temperatures higher than skin temperature.

Advantageous Effects of Invention

According to the present invention, skin condition can be determined. Further, by using thermal sensitivity as an index, skin condition can be classified more closely to the actual condition of the skin compared to when conventional TEWL values are used.

BRIEF DESCRIPTION OF DRAWINGS

FIG. 3 (3) is a scatter graph showing thermal sensitivity (the temperature difference between temperature change sensed temperature and skin temperature) and TEWL values for each group.

FIG. 4 (1) shows the proportion of subjects who perceive their skin condition to be dry in the high thermal sensitivity group and low thermal sensitivity group (1). FIG. 4 (2) and (3) show the degree of skin satisfaction (%) (2) and water content (a.u.) (3) for the high thermal sensitivity group and low thermal sensitivity group.

FIG. 5 is a graph showing the TEWL value (1) and the results of a questionnaire regarding dry skin (2) when thermal sensitivity (the temperature difference (° C.) between temperature change sensed temperature and skin temperature) is classified based on an index.

FIG. 6 is a graph showing the results of a questionnaire regarding dry skin when the TEWL value is classified based on an index.

DESCRIPTION OF EMBODIMENTS

Figure 1:
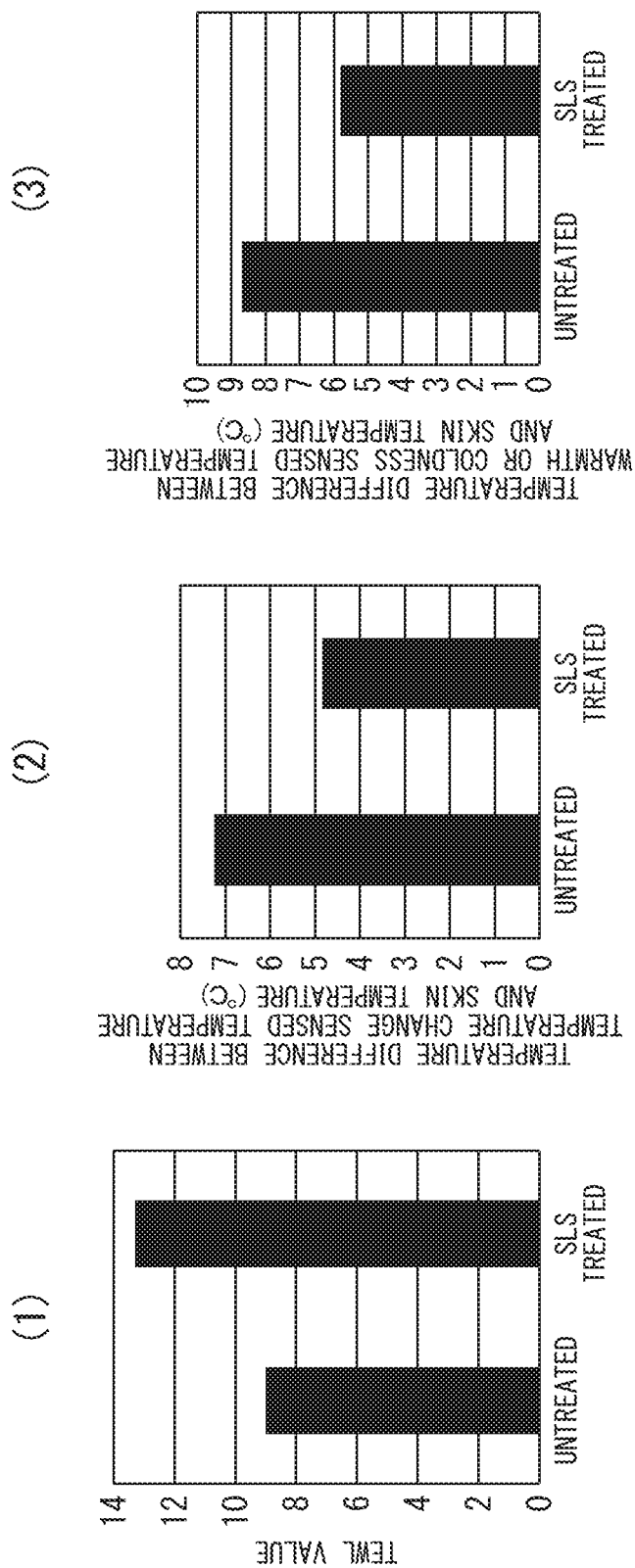
FIG. 1 shows graphs illustrating the TEWL value (1), the temperature difference between temperature change sensed temperature and skin temperature (2), and the temperature difference between warmth or coldness sensed temperature and skin temperature (3) of sodium lauryl sulfate (SLS)-treated sites where slight inflammation was caused and untreated sites on Japanese subjects.

One embodiment of the present invention relates to a method for determining skin condition using thermal sensitivity in skin as an index. The skin condition is determined in the skin of a subject whose skin condition is examined. The skin condition refers to conditions ranging from healthy skin to rough, dry, and inflamed skin. Thermal sensitivity can be correlated with transepidermal water loss. As an example of skin condition, the skin barrier function can be determined.

Sites for determining skin condition can include any part of the skin, for example, skin condition can be determined from skin of the face, arms, back and abdomen. The determination of skin condition of the present invention corresponds to the determination of skin condition from the aesthetic or cosmetic perspective and the methods used therefor may be carried out in beauty salons, cosmetics stores, aesthetic salons, etc., and can be referred to as a non-diagnostic method or a diagnostic assistance method.

Thermal sensitivity can be determined using a measuring device comprising a variable temperature probe. Specifically, a probe set to the skin surface temperature is brought into contact with the skin of a subject, the temperature is changed, and from the temperature at which the subject sensed a temperature change, the thermal sensitivity can be determined. A temperature of 33° C. can usually be used as the skin surface temperature. However, a pre-step of adjusting the probe in contact with the skin to the temperature of the skin may be included since the skin surface temperature can vary depending on the state of the subject, the surrounding environment, and the site of the skin. The pre-step may involve measuring the temperature of the skin with the measuring device and adjusting the temperature of the probe thereto or may involve allowing the temperature of the probe to adjust to the temperature of the skin by providing a sufficient acclimation period.

The temperature difference between the skin temperature and the temperature of the probe at the time of sensing a temperature change can be set as the thermal sensitivity index. Humans sense a temperature change in the skin as a stimulus. Then, humans sense whether the temperature increased or decreased later than the change in temperature. Thus, the time at which simply a temperature change is sensed and the time at which an increase or decrease in the temperature is sensed can be distinguished. The temperature difference between the skin temperature and the temperature of the probe at the time of sensing a temperature change is defined as the temperature difference between temperature change sensed temperature and skin temperature. The temperature difference between the skin temperature and the temperature of the probe at the time of sensing an increase or decrease in temperature is defined as the temperature difference warmth or coldness sensed temperature and skin temperature. Both the temperature difference between temperature change sensed temperature and skin temperature and the temperature difference between warmth or coldness sensed temperature and skin temperature are defined as the sensed temperature difference. The skin condition is determined on the basis of the relationship, preferably the correlation, between the sensed temperature difference and the skin condition. From the viewpoint of determining skin condition more accurately, the change in temperature is preferably an increase in temperature. Such relationships between sensed temperature difference and skin condition can be determined beforehand according to the site on the skin. For example, in various groups of subjects, scatter graphs of TEWL values and sensed temperature can be created in advance for different sites to obtain an approximated curve, and the skin condition can be classified in advance from the sensed temperature. For example, classification can be carried out for every preset temperature, e.g. 1° C., 1.5° C., 2° C., 3° C., or 4° C. In subjects with healthy skin, the sensed temperature difference is about 12° C., so the threshold can be determined according to the number of classification groups (e.g., 6, 5, 4, 3, or 2). For example, if the number of classification groups is 6, classification can be carried out every 2° C. Classification may be carried out using temperature differences of equal intervals or differing intervals.

The TEWL value changes depending on race, age, sex, site, etc. and so it is difficult to say that a specific value or less indicates a healthy skin condition. For a healthy Japanese subject, the TEWL value is typically 10 g/(m$^2$ h) for the cheek and the TEWL value is about 5 g/(m$^2$ h) for the abdomen, back, thigh, and upper arm. In the present invention, without setting any limitations, from among skin conditions, the TEWL value for healthy conditions of the cheek is usually considered to be less than 10. The TEWL value for rough conditions of the cheek is considered to be 12 or more, preferably 14 or more, and more preferably 15 or more.

The variable temperature probe may include a temperature sensor or a Peltier element, and may further include a heat flux sensor. A metal plate having high thermal conductivity, for example, a copper plate may be used for the part of the variable temperature probe that makes contact with the skin. The speed at which the temperature changes may be arbitrarily selected and, for example, may be set to 0.1 to 10.0° C./s. From the viewpoint of reducing measurement times, 0.3° C./s or more is preferable and 0.5° C./s or more is more preferable. From the viewpoint of reducing deviations in temperature change after sensing, 5.0° C./s or less is preferable and 1.0° C./s or less is more preferable.

Another embodiment of the present invention relates to a system for determining skin condition comprising a variable temperature probe, a data processing unit, an input unit, and an output unit. More specifically, the system for determining skin condition comprises executing the following steps:

the probe changes in temperature from a preset temperature;

the input unit receives a signal indicating that a temperature change has been sensed;

the processing unit determines the skin condition on the basis of the temperature of the probe at the time of inputting the signal; and the output unit outputs the skin condition.

The initial temperature of the probe is preferably the skin temperature of the subject, for example, 33° C. may be used. The probe is made to contact the skin and a pre-step of acclimating the temperature of the probe to the skin temperature may be included.

The system is operated by bringing the probe into contact with the skin of a subject. The subject inputs a signal through the input unit when a change in temperature of the probe is sensed. The subject can also input a signal through the input unit when an increase or decrease in temperature is sensed in addition to or instead of when a temperature change is sensed. The processing unit determines the temperature of the probe at the time of inputting a signal from the input unit and determines the skin condition on the basis of the determined temperature. The processing unit calculates the sensed temperature difference between the preset temperature and the temperature that senses temperature change and can determine the skin condition on the basis of the predetermined relationship between the sensed temperature difference and the skin condition. For the relationship between the sensed temperature difference and skin condition, for example, an approximated curve for the scatter graph of the TEWL value and the sensed temperature may be used and predetermined classifications of skin conditions from sensed temperature may also be used.

The system of the present invention may be an integrated device comprising a variable temperature probe, an input unit, a display for the output unit, and a computer for the processing unit, or may be configured with a separate computer. The computer can carry out information processing for determining skin condition. The computer of the present invention comprises a storage unit and a processing unit. Further embodiments of the present invention also relate to a method and program for controlling the system for determining skin condition, and a storage medium for storing the program.

The processing unit can determine the skin condition on the basis of the temperature data at the time of inputting a signal from the input unit and the relationship between temperature and skin condition stored in the storage unit. Specifically, the temperature at the time of the input signal is recorded, the sensed temperature difference from the preset temperature is determined, and the skin condition can be determined from a database of the relationship between the sensed temperature difference and skin conditions stored in the storage unit. The processing unit executes various arithmetic processes based on the program stored in the storage unit. The arithmetic processes are carried out by a processor (e.g., CPU) contained in the processing unit. The processing unit, other than performing the aforementioned arithmetic processes, also contains a function module that controls each of the input unit, the storage unit, the variable temperature probe, and the output unit, and can perform various types of control. Each of these units can be individually configured from an integrated circuit, microprocessor, firmware, or the like. The information regarding skin condition determined by the data processing unit may be temporarily stored in the storage unit or can be directly displayed on the output unit from the data processing unit.

The storage unit includes memory devices such as RAM, ROM and flash memory, fixed disk devices such as hard disk drives, or portable storage devices such as flexible disks and optical disks. The storage unit, in addition to storing data and instructions input from the input unit, the results of arithmetic processes carried out by the processing unit, and the like, also stores programs used in various processes by the computer, and, databases, etc. The computer program may be installed from computer readable media such as a CD-ROM or DVD-ROM or via the internet.

The output unit is configured to output the skin condition obtained by the data processing unit performing arithmetic processes. The output unit may be a display device such as a liquid crystal display or a monitor that directly displays the results of the arithmetic processes, an output means such as a printer, or an interface unit for outputting to an external storage device or for outputting through a network.

The input unit may be, for example, a button that the subject presses when a temperature change is sensed or may be a separate manual input device such as a keyboard or mouse. The input unit may comprise a separate interface unit.

The variable temperature probe configured from a temperature sensor, Peltier element, heat flux sensor, or the like, is controlled by a processing unit. It can change the temperature from a preset temperature at a specified rate, and can also measure the skin temperature using the temperature sensor.

The system of the present invention may perform data processing through an interface unit with a data processing unit on a network. In such cases, data pertaining to the temperature at the time of inputting the input signal from the input unit is transmitted to the data processing unit via the interface unit, the skin condition is determined by the data processing unit, the data pertaining to the skin condition is transmitted via the interface and output on the output unit.

EXAMPLES

Example 1: Treatment Causing Rough Skin in Subjects

The day before measurement, 0.1 to 4.0% sodium lauryl sulfate (SLS) was applied to the skin of the forearm, and a 24-hour patch test was performed. This treatment can be used to cause slight inflammation of the skin. After 24 hours, the patch was removed and the skin was acclimated to 21° C.±2° C. and a humidity of 46±5% for 1 hour. Patch application areas were classified according to ICDRG criteria. A place determined to be "+" by the ICDRG criteria was defined as a weak inflammation site.

Example 2: Measuring Thermal Sensitivity

Figure 2:
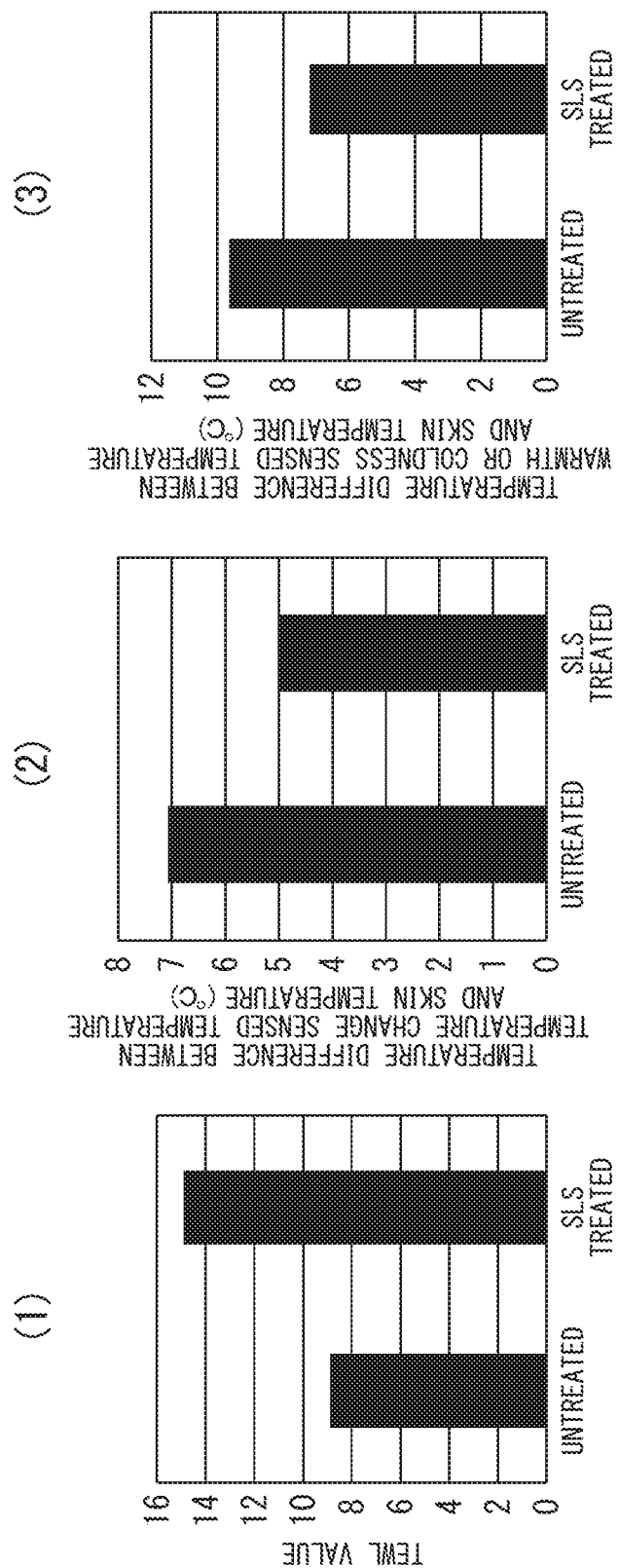
FIG. 2 shows graphs illustrating the TEWL value (1), the temperature difference between temperature change sensed temperature and skin temperature (2), and the temperature difference temperature between warmth or coldness sensed temperature and skin temperature (3) of sodium lauryl sulfate (SLS)-treated sites where slight inflammation was caused and untreated sites on subjects from the four cities of Akita, Beijing, Guangzhou, and Bangkok.

A probe of Thermoception Analyzer Intercross-210 (Intercross corporation) was brought into contact with a weak inflammation site caused by application of a patch and a control site to measure the temperatures of the skin of subjects from four cities (14 from Akita, 12 from Beijing, 13 from Guangzhou, and 22 from Bangkok). The temperature was measured by a probe-side sensor and the temperature control system was used to adjust the heat flux to 0. The temperature at this time was determined to be the skin temperature. The temperature of the probe was changed at a rate of 0.3° C./s. During this process, both the temperatures of the probe at the time the subject sensed the temperature change and at the time the subject sensed an increase or decrease in temperature were recorded. By calculating the temperature differences of the recorded temperatures from the skin temperature, the temperature difference between temperature change sensed temperature and skin temperature and the temperature difference between warmth or coldness sensed temperature and skin temperature. The results of the subjects from Akita and the results of the subjects from the four cities are respectively shown in FIGS. 1 and 2.

Example 3: Determining Relationship Between TEWL Value and Thermal Sensitivity

The relationship between the TEWL value and thermal sensitivity was examined in subjects from seven cities (44 from Akita, 43 from Beijing, 43 from Guangzhou, 47 from Bangkok, 42 from San Francisco, 43 from Lyon, and 49 from Sao Paolo) of six countries. Specifically, the TEWL value was measured using VapoMeter (Delfin) on the cheek of the subject after washing the face. Next, a probe of Thermoception Analyzer Intercross-120 (Intercross) was brought into contact with the same place and in the same manner as previously mentioned, the temperature difference between temperature change sensed temperature and skin temperature and the temperature difference between warmth or coldness sensed temperature and skin temperature were determined.

Figure 3:
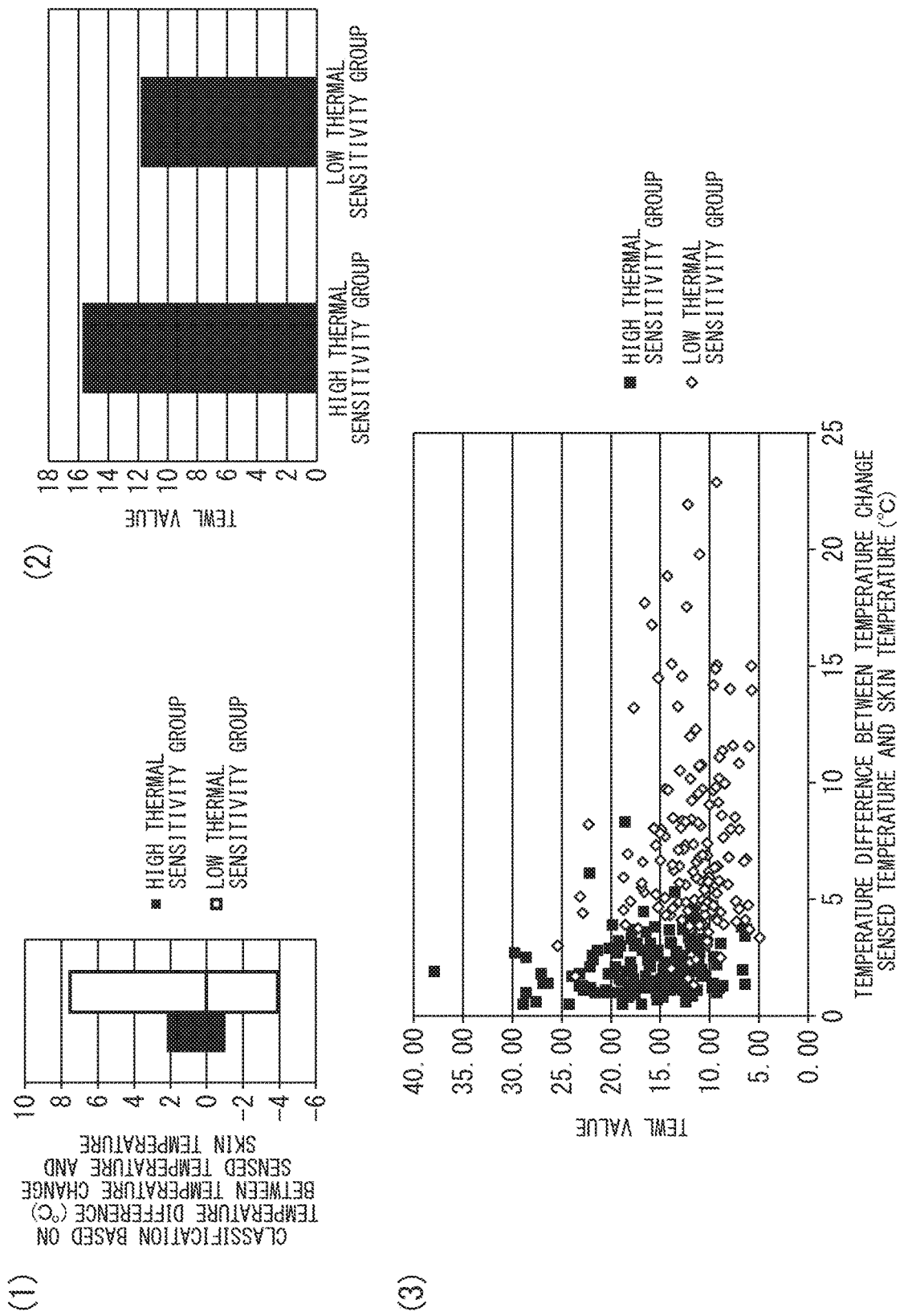
FIG. 3 (1) shows sparse clustering classification into a group with high thermal sensitivity and a group with low thermal sensitivity and (2) shows a graph comparing both groups to TEWL values.

The thermal sensitivity measurement data was analyzed with the analysis software R package "sparcl". Hyperparameters were determined by using the KMeansSparseCluster.permute function, and the hyperparameters were used by the KMeansSparseCluster function for classification into a high thermal sensitivity group and low thermal sensitivity group. Note that the grid search method was used as the method for determining hyperparameters and the candidate value that minimizes the gap statistic was selected. The subjects were categorized as being in either the high thermal sensitivity group or the low thermal sensitivity group (FIG. 3 (1)). For each group, TEWL was compared to reveal that TEWL was significantly high in the high thermal sensitivity group (FIG. 3 (2)). Further, scatter graphs of thermal sensitivity (the temperature difference between temperature change sensed temperature and skin temperature) and TEWL values for each group were created (FIG. 3 (3)).

Figure 4:
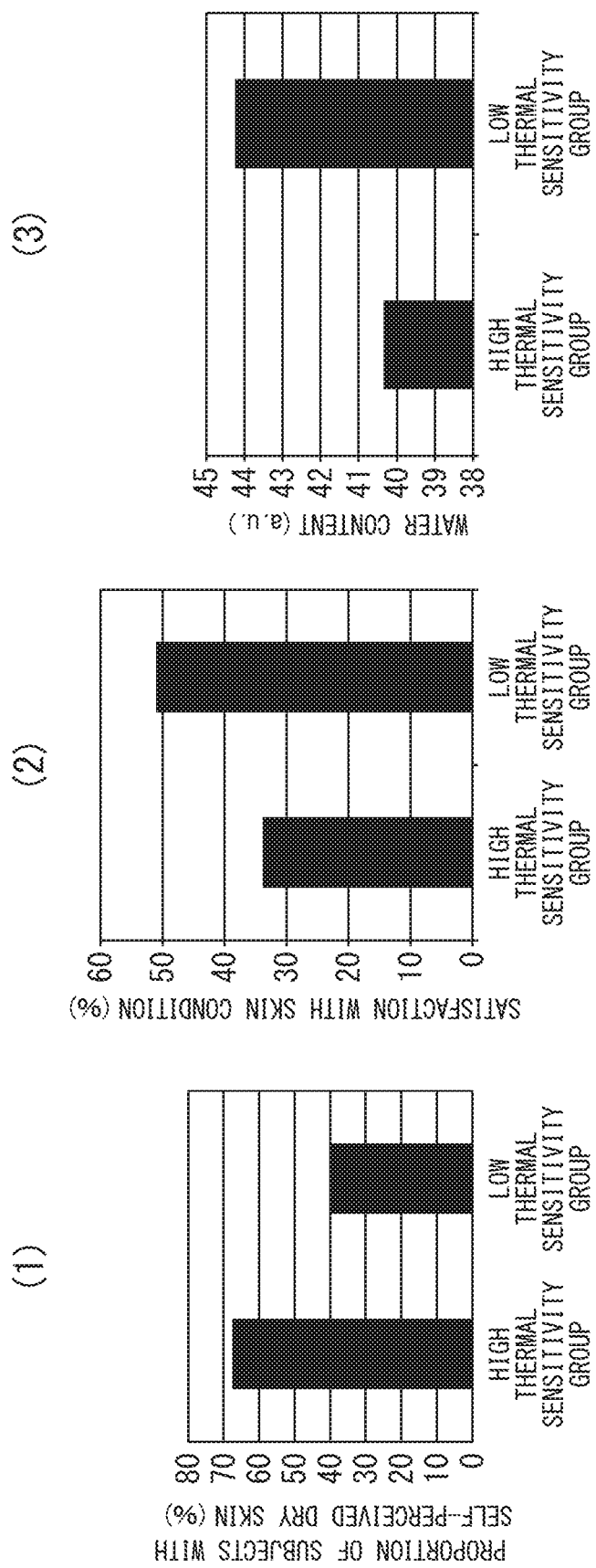
FIG. 4 shows the results of comparing the skin condition of the high thermal sensitivity group and low thermal sensitivity group.

Example 4: Comparing High Thermal Sensitivity Group and Low Thermal Sensitivity Group The subjects were classified into the high thermal sensitivity group and low thermal sensitivity group on the basis of the temperature difference between temperature change sensed temperature and skin temperature and the temperature difference between warmth or coldness sensed temperature and skin temperature determined in EXAMPLE 3, and then the results of a questionnaire regarding dry skin and degree of satisfaction of skin condition of subjects in each group were shown (FIG. 4 (1), (2)). Further, results of measuring the water content of skin were compared (FIG. 4 (3)).

It was revealed that the proportion of subjects who perceived having dry skin was higher and a degree of satisfaction with their skin condition was lower in the high thermal sensitivity group than the low thermal sensitivity group.

Example 5: Relationship Between Classification of Thermal Sensitivity (the Temperature Difference Between Temperature Change Sensed Temperature and Skin Temperature) and Skin Condition On the basis of the experimental results of EXAMPLE 3, the subject groups were classified using the temperature difference between temperature change sensed temperature and skin temperature as an index. Specifically, the temperature difference between temperature change sensed temperature and skin temperature was classified such that the first group was 0 to 2° C., the second group was 2 to 4° C., the third group was 4 to 6° C., etc., up by increments of 2° C. to the sixth group (10 to 12° C.). The average TEWL value for each group was calculated and illustrated in a graph (FIG. 5(1)). Further, the results of the questionnaire regarding dry skin for each group are illustrated (FIG. 5 (2)).

Comparative Example: Relationship Between Classification Using TEWL and Skin Condition As a Comparative Example, on the basis of the experimental results of EXAMPLE 3, the subject groups were classified using TEWL as an index. Specifically, the subjects were classified such that those with a TEWL value of over 20 were in group 1, 15 to 20 were in group 2, 12 to 15 were in group 3, 10 to 12 were in group 4, and 0 to 10 were in group 5. The results of the questionnaire regarding dry skin for each group are illustrated (FIG. 6).

In the classification according to thermal sensitivity in Example 5, the lower the thermal sensitivity, the lower the proportion of subjects with self-perceived dry skin, which showed a relationship between thermal sensitivity and dry skin, whereas classification according to TEWL could not find a relationship with dry skin. Thus, as a method of determining skin condition, it is possible to determine skin condition more closely to the actual skin condition using thermal sensitivity rather than TEWL values.

The invention claimed is:

1. A method for determining a transepidermal water loss value, the method comprising:
   (a) applying a variable temperature probe to an area of a skin of a subject;
   (b) changing a temperature of the variable temperature probe applied to the area of the skin of the subject from a preset temperature value, which is a temperature of the area of the skin of the subject;
   (c) determining a sensed temperature value, which is a value of the temperature of the variable temperature probe applied to the area of the skin of the subject, at which value the subject senses the changing;
   (d) calculating a sensed temperature difference for the area of the skin of the subject as a difference between the sensed temperature value and the preset temperature value; and
   (e) determining a transepidermal water loss in the area of the skin of the subject based on the calculated sensed temperature difference for the area of the skin of the subject from a pre-determined relationship between a transepidermal water loss and a sensed temperature difference for a population of subjects for the same skin area, wherein the predetermined relationship provides a transepidermal water loss value for each of a plurality of temperature difference intervals; and wherein said determining (e) further comprises identifying a temperature difference interval among said plurality to which the sensed temperature difference belongs, and assigning a transepidermal water loss value that corresponds to the identified temperature difference interval according to the predetermined relationship as a value of the transepidermal water loss in the area of the skin of the subject.

2. The method of claim 1, wherein the area of the skin is selected from a face skin, a back skin and an abdomen skin.

3. The method of claim 1, wherein the changing is increasing the temperature of the variable temperature probe applied to the area of the skin of the subject.

4. A system for determining a transepidermal water loss value, the system comprising a variable temperature probe, a data processing unit, an input unit and an output unit, wherein
   the probe is configured to change a temperature of the probe from a preset temperature value when applied to an area of a skin of a subject;
   the input unit is configured to receive a signal from the subject when the subject senses the change in the temperature of the probe applied to the area of the skin of the subject, while recording the temperature of the probe at that time as a sensed temperature value;
   the data processing unit is configured to calculate a sensed temperature difference for the area of the skin of the subject as a difference between the sensed temperature value and the preset temperature value and to determine a transepidermal water loss in the area of the skin of the subject based on the calculated sensed temperature difference for the area of the skin of the subject from a pre-determined relationship between a transepidermal water loss and a sensed temperature difference for a population of subjects for the same skin area, wherein the predetermined relationship provides a transepidermal water loss value for each of a plurality of temperature difference intervals; and wherein said determining of transepidermal water loss further comprises identifying a temperature difference interval among said plurality to which the sensed temperature difference belongs, and assigning a transepidermal water loss value that corresponds to the identified temperature difference interval according to the predetermined relationship as a value of the transepidermal water loss in the area of the skin of the subject; and
   the output unit is configured to output the value of the determined transepidermal water loss in the area of the skin of the subject.

5. The system of claim 4, wherein the preset temperature value is a temperature of the area of the skin of the subject.

6. The system of claim 4, wherein the probe is configured to increase the temperature from the preset temperature value when applied to an area of a skin of a subject.

7. The system of claim 4, further comprising a storage unit configured to store the pre-determined relationship.

* * * * *